United States Patent [19]

Misselbrook

[11] Patent Number: 4,511,395

[45] Date of Patent: Apr. 16, 1985

[54] METHOD FOR THE PREPARATION OF WATER DISPERSIBLE GRANULAR HERBICIDAL COMPOSITIONS WITH INCREASED THERMAL STABILITY

[75] Inventor: John Misselbrook, Lambertville, N.J.

[73] Assignee: American Cyanamid Company, Stamford, Conn.

[21] Appl. No.: 451,140

[22] Filed: Dec. 20, 1982

[51] Int. Cl.³ .............................................. A01N 25/22
[52] U.S. Cl. .................................. 71/121; 71/DIG. 1
[58] Field of Search ........................... 71/DIG. 1, 121

[56] References Cited

U.S. PATENT DOCUMENTS 4,082,537  4/1978  Dudkowski ............................ 71/121
4,289,525  9/1981  Pasarela et al. ......................... 71/92

FOREIGN PATENT DOCUMENTS 2037585A  11/1979  United Kingdom .

*Primary Examiner*—Catherine L. Mills
*Attorney, Agent, or Firm*—E. J. Tsevdos; A. R. Noë

[57]  ABSTRACT

The present invention relates to a process for the preparation of water dispersible granular herbicidal compositions with increased thermal stability, which contain low melting substituted dinitroaniline compounds.

11 Claims, No Drawings

METHOD FOR THE PREPARATION OF WATER DISPERSIBLE GRANULAR HERBICIDAL COMPOSITIONS WITH INCREASED THERMAL STABILITY

The present invention relates to a method for the preparation of water-dispersible granular compositions containing dinitroaniline herbicides of structural formula (I)

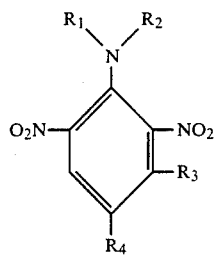

wherein $R_1$ is selected from H, $C_1$-$C_4$ straight or branched-chain alkyl, $C_3$-$C_4$ alkenyl and $C_3$-$C_4$ alkynyl; $R_2$ is selected from $C_1$-$C_6$ straight or branched-chain alkyl and optionally substituted with Cl or $OCH_3$, $C_3$-$C_4$ alkenyl, and $C_3$-$C_4$ alkynyl; $R_3$ is H, $CH_3$ or $CH_2OCH_3$; $R_4$ is $C_1$-$C_4$ alkyl, $CF_3$ or Cl; and said compositions are characterized by improved storage stability at elevated temperatures.

A number of formula (I) herbicides, such as N-(1-ethylpropyl)-2,6-dinitro-3,4-xylidine are highly sought after for the selective control of certain grasses in the presence of agricultural crops; while some of the compounds of formula (I) are efficacious for the control of broadleaf weeds.

Customarily, such herbicides may be formulated as wettable powders, dispersible granulars, emulsifiable concentrates, flowables, and the like. Of these, the dispersible granular formulations offer ease of handling coupled with reduced dusting, and of course, the absence of an organic, flammable and possible toxic solvent that would be present if an emulsifiable concentrate were used instead.

Unfortunately, however, conventional dispersible granular compositions (or wettable powders) containing formula (I) dinitroaniline herbicides which are solid at room temperature but have melting points below 100° C., have a tendency to cake, fuse or lump up when stored at or exposed to elevated temperatures, due to the excessive softening or partial melting of said formula (I) herbicides. In general the above referred-to conventional compositions are prepared by blending and milling the appropriate amount of the selected formula (I) dinitroaniline herbicide, a conventional inert carrier and one or more wetting and/or dispersing agent(s), followed by granulating said blend in the appropriate equipment using a binder solution as the granulating agent.

A currently available method for the preparation of wettable powder compositions of said low melting compounds is exemplified by U.K. Patent Application No. 2,037,585A which describes the preparation of compositions containing moderate quantities (10-50%) and preferably (15-30%) of a low melting herbicide. However, this method requires the use of specific specially treated silica derivatives in order to prepare stable compositions as indicated below.

A suitable choice of silica derivative must be made in order to overcome caking in the formulation. Not all silicas can be employed for this purpose and the efficacy of the silica material appears not only to depend on its physical properties but also to be related to its chemical nature, the effect being limited to fumed or precipitated silicas. A mixture of fumed and precipitated silicas may, of course, be employed. Other silica materials which are widely used in herbicide formulations such as precipitated silicates and micronised silica are not effective for the purpose.

Fumed silica is the product of burning silicon tetrachloride ($SiCl_4$) in an atmosphere of oxygen and hydrogen. The average particle diameter of the resulting material is generally within the range of 2 to 50 millimicrons and the surface area between 175 and 400 square meters per gram, as measured by the Brunauer, Emmett and Teller equation [J. Amer. Chem. Soc., 60:309 (1938)]. Precipitated silica may be prepared by chemical reaction of an alkali metal silicate, such as for example sodium silicate, with mineral acid such as for example hydrochloric acid, followed by adjustment of the pH to cause precipitation. The precipitate is then separated, washed and dried. Its particle size is generally within the range of 5 to 50 millimicrons and its surface area between 50 and 350 square meters per gram.

Preferably the composition also comprises a solid inert carrier which can be any of the materials well known in the art for preparing solid herbicidal formulations and these include, for example, kaolin, talc, montmorillonite, attapulgite, diatomaceous earth and hydrated sodium silicoaluminate.

We now find, that by the method of the present invention dispersible granular and wettable powder compositions containing high concentrations (up to 70%) of low melting pesticidal compounds may be prepared utilizing naturally occurring swelling hydrous aluminum silicate clays which remain free-flowing and do not agglomerate, lump-up or fuse when stored at, or are exposed to elevated temperatures in the range of about 50° C. for a prolonged period of time.

The finding that certain naturally occurring swelling clays, are suitable for preparing heat-stable wettable powder, and dispersible granular compositions, containing high concentrations (50-70% by weight), of low melting materials is unexpected. Lower concentration compositions may also be prepared as can mixtures of active ingredients.

Further, said heat stable compositions may be prepared at ambient temperatures by the method of the present invention. Prior methods for preparing heat stable compositions of low-melting materials required impregnation of the low-melting active ingredient, either in a solvent, which subsequently had to be removed, or as a melt, onto sufficient quantities of specially treated silica derivatives to absorb all the materials as stated above.

While the present invention provides a method for preparing heat-stable compositions of low-melting materials at ambient temperatures, these compositions may also be prepared at elevated temperatures if for some reason this is desirable, as is the case with the substituted N,N-dialkyl-2,6-dinitroaniline herbicides.

Naturally-occurring swelling clays suitable for use in said compositions may be described as hydrous, sodium and magnesium aluminum silicates having a montmorillonite unit cell structure. The montmorillonite unit cell has two silicon-oxygen sheets with an aluminum hydroxyl sheet sandwiched between them. Montmorillonite is described as a "Si-Al-Si" structure.

Commercially available, naturally occurring swelling clays include VOLCLAY® Wyoming Bentonites, VEEGUM®, or other naturally occurring swelling clays which contain the same montmorillonite unit structure and properties.

Thus, from about 20 to 70% by weight (preferably 30-60%) of a dinitroaniline of formula (I) is admixed with from 20-87.5% by weight of a swelling bentonite, 2-7.5% by weight of a wetting agent, 2-6% by weight of a dispersing agent, and up to 7.5% by weight of a precipitated silica either at ambient or, if so desired, at elevated temperatures wherein said formula (I) herbicides are melting, until a homogeneous mixture is obtained.

The mixture obtained is passed through a milled fitted with a 1/16 to ¼ inch screen followed by air milling at 100-105 psi to a particle size 5 to 10 μm.

If a wettable powder is desired, this material is then blended with 0.25-1.0% of a hydrophobic silica powder and packaged.

If a dispersable granule is desired, the above milled mixture is wet agglomerated with a granulating blender, dried at 50° C. to contain less than 2% water and is then passed through a screen to obtain the desired fraction of 10 to 60 mesh size range.

This mixture is blended with 0.25-1.0% by weight of a hydrophobic silica power to aid in maintaining the free-flow characteristics of the mixture and is then packaged.

Thus, the preparation of a typical formulation of the present invention may be illustrated as follows: 65.87% by weight of flaked technical N-(1-ethylpropyl)-2,6-dinitro-3,4-xylidine containing 1.1% by weight of sodium dioctylsuccinate (92% active ingredient) is admixed at ambient temperature with 22% by weight of a naturally occurring swelling bentonite clay, 5% by weight of sodium N-methyl-n-oleyl taurate, 2.5% by weight of sodium naphthalene sulfonate condensate and 4% by weight precipitated silica until the mixture is homogeneous.

This mixture is passed through a mill fitted with a 1/16 inch to ¼ inch screen and then through an air mill at 100-105 psig to a particle size of 5 to 10 μm.

The thus-obtained powder is tumbled in a suitable granulator and wet-agglomerated with water. The granules are then dried at 50° C. to contain less than 2% moisture, separated to the desired size range of from 10 to about 60 mesh, and coated with from about 0.25% to about 1.0% of fumed hydrophobic silica.

The present invention is further illustrated by the following non-limiting examples.

EXAMPLE 1

Evaluation of dispersible granular formulations of dinitroaniline herbicides prepared by the method of the invention The dinitroaniline herbicide containing sodium dioctylsulfosuccinate is admixed at the desired temperature with a swelling bentonite, sodium N-methyl-N-oleyl-taurate, sodium naphthalene sulfonate condensate and precipitated silica, until homogeneous.

The mixture is milled through a 1/16 to ¼ inch screen and then through an air mill at 100-105 psig to a particle size of 5 to 10 μm.

This power is wet-agglomerated with water in a suitable granulation blender and then dried to contain less than 2% water. The desired fraction 10 to 60 mesh size range is collected by screening and coated with a fumed hydrophobic silica. The composition of the formulations is given in Table I below.

A series of comparative formulations prepared by the same method with other naturally occurring clays which are non-swelling is given in Table II below.

TABLE I

Compositions of granular and wettable powder compositions utilizing swelling clays

| No | % Active Ingredient | Active Ingredient | % Sodium dioctylsulfo-succinate | % Swelling clay | % N—methyl-n-oleyl taurate | % Sodium naphthalene sulfonate | % Precipitated silica | % Fumed silica |
|---|---|---|---|---|---|---|---|---|
| 1 | 60.0 | N—(1-ethylpropyl)-2,6-dinitro-3,4-xylidine | 0.72 | 22.0 | 5.0 | 2.5 | 1.9 | 0.25 |
| 2 | 60.0 | N—(1-ethylpropyl)-2,6-dinitro-3,4-xylidine | 0.72 | 25.8 | 5.0 | 2.5 | 0 | 0.25 |
| 3 | 55.0 | N—(1-ethylpropyl)-2,6-dintro-3,4-xylidine | 0.66 | 22.0 | 5.0 | 2.5 | 4.7 | 0.25 |
| 4 | 52.5 | N—(1-ethylpropyl)-2,6-dinitro-3,4-xylidine | 0.63 | 22.0 | 5.0 | 2.5 | 6.1 | 0.25 |
| 5 | 50.0 | N—(1-ethylpropyl)-2,6-dinitro-3,4-xylidine | 0.60 | 22.0 | 5.0 | 2.5 | 7.5 | 0.25 |
| 6 | 60.0 | α,α,α-trifluoro-2,6-dinitro-N,N—dipropyl-p-toluidine | 0 | 22.0 | 5.0 | 2.5 | 5.3 | 0.25 |

TABLE II

Compositions of comparative granular and wettable powder compositions utilizing non-swelling clays

| No | % Active Ingredient | Active Ingredient | % Sodium dioctylsulfo-succinate | % Non-Swelling clay/type | % N—methyl-n-oleyl taurate | % Sodium naphthalene sulfonate | % Precipitated silica | % Fumed silica |
|---|---|---|---|---|---|---|---|---|
| 1' | 60.0 | N—(1-ethylpropyl)- | 0.72 | 22.0 | 5.0 | 2.5 | 5.3 | 0.25 |

TABLE II-continued

Compositions of comparative granular and wettable powder compositions utilizing non-swelling clays

| No | % Active Ingredient | Active Ingredient | % Sodium dioctylsulfo-succinate | % Non-Swelling clay/type | % N—methyl-n-oleyl taurate | % Sodium naphthalene sulfonate | % Precipitated silica | % Fumed silica |
|---|---|---|---|---|---|---|---|---|
| 1″ | 60.0 | 2,6-dinitro-3,4-xylidine N—(1-ethylpropyl)-2,6-dinitro-3,4-xylidine | 0.72 | kaolin 22.0 | 5.0 | 2.5 | 5.3 | 0.25 |
| 1‴ | 60.0 | N—(1-ethylpropyl)-2,6-dinitro-3,4-xylidine | 0.72 | non-swelling bentonite 22.0 Attapulgite | 5.0 | 2.5 | 5.3 | 0.25 |

EXAMPLE 2

Evaluation of suspensibility of heat stressed wettable powder compositions

A 5.0 g sample of the appropriate composition is mixed with 50 mL water, the mixture stirred for 30 second and is then transferred to a 100 mL volume and mixed thoroughly by inverting the cylinder end over end 30 times at the rate of one complete cycle every two seconds. The graduated cylinder is then allowed to stand in a water bath for 0.5 hours at 30° C. A 25 mL aliquot is then removed from approximately the middle of the graduated cylinder and evaporated to dryness. The residue is weighed and from the data obtained the percent suspension is calculated. Another sample of the suspension is filtered through a wet, 200 mesh screen to determine the percent retention. These tests are run with standard hard water designed to provide a hardness of 345 ppm calculated as calcium carbonate [having the following composition: 0.304 g $CaCL_2$ and 0.139 g $MgCl_2.6H_2O$ per 1000 mL $H_2O$]. The results obtained are given in Table III below.

TABLE III

Evaluation of the suspensibility of heat stressed wettable powder compositions of the invention and comparative compositions in standard hard water

| Clay type | Composition | Determination of | Un-stressed | Stressed at 50° C. |
|---|---|---|---|---|
| Swelling | 1 | % Suspensibility | 93.4 | 91.0 |
| | | % Wet sieve retention | <0.1 | 0.23 |
| Non-swelling | 1′ | % Suspensiblity | 96.2 | 79.2 |
| | | % Wet sieve retention | 0.87 | 3.06 |
| Non-swelling | 1″ | % Suspensibility | 93.8 | 59.22 |
| | | % Wet sieve retention | 0.78 | 4.16 |
| Non-swelling | 1‴ | % Suspensibility | 95.9 | 76.0 |
| | | % Wet sieve retention | 0.67 | 0.87 |

It can be seen from Table III above that wettable powder compositions of the invention suspend well in hard water after being subjected to heat stress, while similar compositions prepared with naturally occurring non-swelling of clays do not.

EXAMPLE 3

Dispersibility of granular compositions

A 10.0 g sample of the appropriate composition is stirred at 350–400 rpm with 200 mL of standard hard water at 5° C. A 10 mL aliquot is taken from the test system at 30 seconds, 1 minute, 2 minutes and 3 minutes; each sample is then filtered through a 100 mesh filtering system and transferred into a petri dish and dried to constant weight at 50° C. and the weight recorded. This procedure is replicated three times for each composition and the percentage of each sample dispersed at each time interval is then calculated.

The results of these tests are reported in Table IV below, from which it can be seen that the granular compositions of the present invention exhibit superior dispersability to that of the comparative examples prepared with non-swelling clays.

TABLE IV

Comparative percentage disintegration of granular compositions utilizing swelling clays and non-swelling clays

| Type of Clay | Composition Number | Percent Disintegration | | | |
|---|---|---|---|---|---|
| | | 30 sec | 1 min | 2 min | 3 min |
| Swelling | 1 | 81.9 | 93.5 | 96.4 | 98.7 |
| Non-swelling | 1′ | 8.0 | 8.0 | 17.0 | 17.0 |
| Non-swelling | 1″ | 8.0 | 6.1 | 7.9 | 14.7 |
| Non-swelling | 1‴ | 6.0 | 9.8 | 9.8 | 13.2 |
| Swelling | 2 | 75.3 | 89.7 | 96.2 | 97.1 |
| Swelling | 3 | 79.3 | 93.6 | 96.1 | 97.0 |
| Swelling | 4 | 79.0 | 94.8 | 96.0 | 96.2 |
| Swelling | 5 | 89.7 | 87.7 | 94.5 | 98.7 |
| Swelling | 6 | 30.0 | 66.1 | 91.3 | 96.4 |

What is claimed is:

1. A method for the preparation of heat stable water-dispersible granular compositions, said method comprising: melting about 50% to 70%, by weight, of a low-melting substituted compound of structural formula (I),

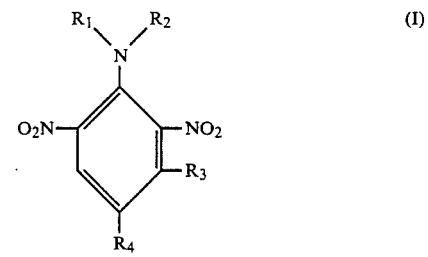

wherein $R_1$ is hydrogen, $C_1$–$C_4$ straight or branched-chain alkyl, $C_3$–$C_4$ alkenyl or $C_3$–$C_4$ alkynyl; $R_2$ is $C_1$–$C_6$ straight or branched-chain alkyl and optionally substituted with Cl or $OCH_3$, $C_3$–$C_4$ alkenyl or $C_3$–$C_4$ alkynyl; $R_3$ is hydrogen, $CH_3$ or $CH_2OCH_3$; $R_4$ is $C_1$–$C_4$ alkyl, $CF_3$ or Cl; mixing with said melt, on a weight basis, 0.0% to 3% sodium dioctyl sulfosuccinate; 2% to 7.5% of a wetting agent selected from sodium N-methyl-N-oleoyltaurate, octylphenoxy polyethoxy ethanol and nonylphenoxy polyethoxy ethanol; 2% to 6% of a dispersing agent selected from sodium lignin sulfonate and the sodium salt of a naphthalene sulfonic acid-formaldehyde condensate; 0.0% to 7.5% of a hydrophilic precipitated silica; and naturally occurring swelling hydrous aluminum silicate clay, in amounts sufficient to total the composition to 100%; cooling the thus-obtained composition; milling said composition to a particle size range of 5 μm to 10 μm; and granulating same with water.

2. A method for the preparation of heat-stable water-dispersible granular compositions, said method comprising: admixing, on a weight basis, at ambient temperature, about 20% to 70% of a low melting-substituted compound of the structural formula,

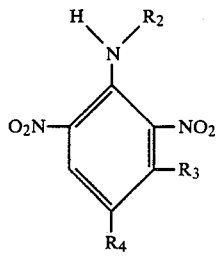

wherein $R_2$ is $C_1$–$C_6$ straight or branched-chain alkyl and optionally substituted with Cl or $OCH_3$, $C_3$–$C_4$ alkenyl or $C_3$–$C_4$ alkynyl; $R_3$ is hydrogen, $CH_3$ or $CH_2OCH_3$; $R_4$ is $C_1$–$C_4$ alkyl, $CF_3$ or Cl; with 1% to 3% sodium dioctyl sulfosuccinate; 2% to 7.5% of a wetting agent selected from sodium N-methyl-N-oleoyltaurate, octylphenoxy polyethoxy ethanol and nonylphenoxy polyethoxy ethanol; 2% to 6% of a dispersing agent selected from sodium lignin sulfonate and the sodium salt of a naphthalene sulfonic acid-formaldehyde condensate; 0.0% to 7.5% of a hydrophilic precipitated silica; and naturally occurring swelling hydrous aluminum silicate clay, in amounts sufficient to total the composition to 100%; milling said composition to a particle size range of 5 μm to 10 μm; and granulating same with water.

3. A method according to claim 1, wherein said formula (I) compound is N-(1-ethylpropyl)-2,6-dinitro-3,4-xylidine, α,α,α-trifluoro-2,6-dinitro-N,N-dipropyl-p-toluidine, or N-butyl-N-ethyl-α,α,α-tri-fluoro-2,6-dinitro-p-toluidine and comprises 50% to 70%, by weight, of the composition.

4. A method according to claim 1, wherein on a weight basis 50% to 60% α,α,α-trifluoro-2,6-dinitro-N,N-dipropyl-p-toluidine is melted with 2.5% to 7.5% of the wetting agent sodium N-methyl-N-oleoyltaurate, 2.0% to 6% of the dispersing agent sodium salt of naphthalene sulfonic acid-formaldehyde condensate; the precipitated silica is used in amounts of 0.0% to 7.5%; and the swelling clay is used in amounts sufficient to total the formulation to 100%.

5. A method according to claim 2, excepting that 0.25 to 1.0% by weight of fumed silica is used to coat the granules and the amount of swelling clay used is lowered by this amount.

6. A method according to claim 2, wherein said formula (I) compound is N-(1-ethylpropyl)-2,6-dinitro-3,4-xylidine, and comprises 30 to 70% by weight of the formulation.

7. A method according to claim 2, wherein on a weight basis 40 to 60% N-(1-ethylpropyl)-2,6-dinitro-3,4-xylidine, containing 1.1 to 2.5% by weight of sodium dioctyl sulfosuccinate, is admixed with 2.5 to 7.5% of the wetting agent sodium N-methyl-N-oleoyltaurate, 2.0 to 6.0% of the sodium salt of naphthalene sulfonic acid-formaldehyde condensate; the precipitated silica is used in amounts of 0.0 to 7.5% by weight; the swelling clay is used in amounts sufficient to total the formulation to 100%.

8. A method according to claim 2, excepting that 0.25 to 1.0% by weight of fumed silica is used to coat the granules and the amount of swelling clay used is lowered by the amount.

9. A method according to claim 2, wherein the amount of N-(1-ethylpropyl)-2,6-dinitro-3,4-xylidine is 60% the amount of sodium dioctyl sulfosuccinate is 1.1%; the amount of swelling clay is 22.0%; the amount of precipitated silica is 3.6%; the amount of sodium N-methyl-N-oleoyltaurate is 5% and the amount of the sodium salt of naphthalene sulfonic acid-formaldehyde condensate is 2.5%.

10. A water-dispersible, heat-stable granular composition with a 10 to 60 mesh size range, said composition comprising, on a weight basis: an intimate mixture of 50% to 70% of a low melting substituted active compound, said compound having a melting point below 100° C. and having structural formula (I),

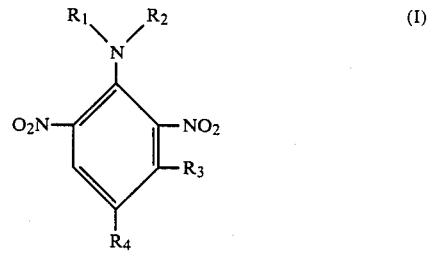

wherein $R_1$ is hydrogen, $C_1$–$C_4$ alkyl straight chain or branched, $C_3$–$C_4$ alkenyl or $C_3$–$C_4$ alkynyl; $R_2$ is $C_1$–$C_6$ alkyl straight chain or branched and optionally substituted with Cl or $OCH_3$, $C_3$–$C_4$ alkenyl or $C_3$–$C_4$ alkynyl; $R_3$ is hydrogen, $CH_3$ or $CH_2OCH_3$; $R_4$ is $C_1$–$C_4$ alkyl, $CF_3$ or Cl; 0.0% to 3% sodium dioctyl sulfosuccinate; 2% to 7.5% of a wetting agent selected from sodium N-methyl-N-oleoyltaurate, octylphenoxy polyethoxy ethanol and nonylphenoxy polyethoxy ethanol; 2% to 6% of a dispersing agent selected from sodium lignin sulfonate and the sodium salt of a naphthalene sulfonic acid-formaldehyde condensate; 0.0% to 7.5% of a hydrophilic precipitated silica; 0.0% to 1.0% of a fumed silica; and naturally occurring swelling hydrous aluminum silicate clay, in amounts sufficient to total the composition to 100%.

11. A heat-stable wettable powder composition comprising, on a weight basis: an intimate mixture of 50% to 70% of a low melting active compound, having a melting point below 100° C. and having structural formula (I),

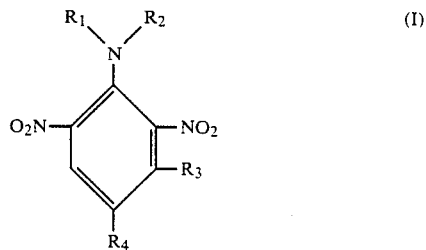

wherein $R_1$ is hydrogen, $C_1$–$C_4$ alkyl straight chain or branched, $C_3$–$C_4$ alkenyl or $C_3$–$C_4$ alkynyl; $R_2$ is $C_1$–$C_6$ alkyl straight chain or branched and optionally substituted with Cl or OCH$_3$, C$_3$–C$_4$ alkenyl or C$_3$–C$_4$ alkynyl; R$_3$ is hydrogen, CH$_3$ or CH$_2$OCH$_3$; R$_4$ is C$_1$–C$_4$ alkyl, CF$_3$ or Cl; 0.0% to 3% sodium dioctyl sulfosuccinate; 2% to 7.5% of a wetting agent selected from sodium N-methyl-N-oleoyltaurate, octylphenoxy polyethoxy ethanol and nonylphenoxy polyethoxy ethanol; 2% to 6% of a dispersing agent selected from sodium lignin sulfonate and the sodium salt of a naphthalene sulfonic acid-formaldehyde condensate; 0.0% to 7.5%, by weight, of a hydrophilic precipitated silica; and naturally occurring swelling hydrous aluminum silicate clay, in amounts sufficient to total the composition to 100%.

* * * * *